(12) United States Patent
Jurak et al.

(10) Patent No.: US 11,517,243 B2
(45) Date of Patent: Dec. 6, 2022

(54) METHOD OF ELECTROCARDIOGRAPHIC SIGNAL PROCESSING AND APPARATUS FOR PERFORMING THE METHOD

(71) Applicants: Institute of Scientific Instruments of the Czech Academy of Sciences, v. v. i., Brno (CZ); St. Anne's University Hospital Brno, Brno (CZ); Charles University, Prague (CZ); CARDION s.r.o., Brno (CZ)

(72) Inventors: Pavel Jurak, Brno (CZ); Josef Halamek, Brno (CZ); Ivo Viscor, Brno (CZ); Filip Piesinger, Brno (CZ); Vlastimil Vondra, Brno (CZ); Radovan Smisek, Kurim (CZ); Pavel Leinveber, Policka (CZ); Magdalena Matejkova, Nemsova (SK); Jolana Lipoldova, Brno (CZ); Miroslav Novak, Brno (CZ); Karol Curila, Prague (CZ); Jana Vesela, Upice (CZ); Frits W. Prinzen, Maastricht (NL); Ivo Nekuda, Brno (CZ); Vit Nekuda, Brno (CZ)

(73) Assignees: INSTITUTE OF SCIENTIFIC INSTRUMENTS OF THE CZECH ACADEMY OF SCIENCES, V. V. I., Brno (CZ); ST. ANNE'S UNIVERSITY HOSPITAL BRNO, Brno (CZ); CHARLES UNIVERSITY, Prague (CZ); CARDIAN S.R.O., Prague (CZ)

( * ) Notice: Subject to any disclaimer, the term of this patent is extended or adjusted under 35 U.S.C. 154(b) by 0 days.

(21) Appl. No.: 17/104,928

(22) Filed: Nov. 25, 2020

(65) Prior Publication Data
US 2021/0161457 A1 Jun. 3, 2021

(30) Foreign Application Priority Data

Nov. 29, 2019 (EP) .................................. 19212534

(51) Int. Cl.
*A61B 5/366* (2021.01)
*A61B 5/339* (2021.01)
(Continued)

(52) U.S. Cl.
CPC .............. *A61B 5/366* (2021.01); *A61B 5/308* (2021.01); *A61B 5/339* (2021.01); *A61B 5/271* (2021.01)

(58) Field of Classification Search
CPC ......... A61B 5/366; A61B 5/352; A61B 5/349; A61B 5/346
See application file for complete search history.

(56) References Cited

U.S. PATENT DOCUMENTS 9,949,655 B2* 4/2018 Jurak ................... A61B 5/7253

OTHER PUBLICATIONS

F. Plesinger et al. Circulation: Arrhythmia and Electrophysiology. 2018;11:e005719, originally published Apr. 26, 2018, https://doi.org/10.1161/CIRCEP.117.005719, retrieved Nov. 25, 2020.

(Continued)

*Primary Examiner* — George R Evanisko
(74) *Attorney, Agent, or Firm* — Notaro, Michalos & Zaccaria P.C.

(57) ABSTRACT

A method of processing of electrocardiogram includes the steps of providing an electrocardiogram comprising signals in at least two channels; selecting at least two frequency ranges of the signal in each of the said at least two channels; calculating an envelope for the signal in each frequency range in each channel; dividing the calculated envelope of the signal in each frequency range in each channel into QRS complex segment envelopes; and computing an average or (Continued)

median envelope as an average or mean of QRS complex segment envelopes for each frequency range in each channel.

18 Claims, 16 Drawing Sheets

(51) Int. Cl.
*A61B 5/308* (2021.01)
*A61B 5/271* (2021.01)

(56) References Cited

OTHER PUBLICATIONS

Halamek J, et al., Plos One May 2019, https://doi.org/10.1371/journal.pone.0217097, retrieved Nov. 25, 2020.

* cited by examiner

METHOD OF ELECTROCARDIOGRAPHIC SIGNAL PROCESSING AND APPARATUS FOR PERFORMING THE METHOD

TECHNICAL FIELD OF THE INVENTION

The present invention relates to a method of processing of broad-band multi-channel electrocardiogram (ECG) and to an apparatus for carrying out the method. The results obtained from the processing method allow to determine electrical activation properties of heart ventricles.

BACKGROUND ART

Devices for recording electrical activity of heart, electrocardiogram or ECG, are commonly used in cardiology for heart disease diagnostic. Standard ECG monitors provide an ECG output signal in a frequency range of up to about 100 Hz. High-resolution ECG monitors with a higher sampling rate 1-4 kHz are available on the market to a limited extent. State of art of high-frequency ECG analysis is described in the study of Guy Amit, et al., Journal of Electrocardiology, 2014;47(4):505-511. Morphology of the QRS complex in the band from 150 up to 250 Hz, i. e. centralization, conceivably broadening and bifurcation of amplitude peaks, often defined by means of RAZ (Reduced Area Zone) parameters, serves for diagnostics of pathological phenomena in myocardium, in particular of ischemic heart disease.

Recently, the inventors applied high-frequency electrocardiography (HF-ECG, 150-350 Hz) to compute ventricular electrical delay (VED) determined in 676 left bundle branch block (LBBB) patients—F Plesinger et al. Circulation: Arrhythmia and Electrophysiology. 2018;11:e005719, originally published Apr. 26, 2018, https://doi.org/10.1161/CIRCEP.117.005719. The results showed that VED predicts survival in biventricular resynchronization patients in a more reliable manner than the conventional QRS-derived parameters. A more recent study indicated that VED might be a more useful predictor for cardiac resynchronization therapy response than ECG characteristics of strict LBBB, Halamek J, et al., Plos ONE May 2019, https://doi.org/10.1371/journal.pone.0217097. The concept with a single-band ultra-high-frequency (500-1000 Hz) 12-lead ECG by Jurak P et al., J Interv Card Electrophysiol. 2017; 49(3): 245-254 presented measures of electrical depolarization patterns and ventricular electrical dyssynchrony. Method of measuring and analyzing the ultra-high-frequency signals of myocardial activity and their processing to time numerical parameters that describe the electrical ventricular dyssynchrony was described by the inventors in the U.S. Pat. No. 9,949,655.

The aim of the present invention is to provide a method and an apparatus for processing of signals obtained from broad-band ultra-high-frequency oscillations generated by myocardium (UHF-ECG), i.e. the ECG components in frequency ranges within the 100-1000 Hz range, which would allow to accurately identify time distribution of ventricular depolarization in order to reliably diagnose heart abnormalities and pathologies which can effectively be treated by cardiac pacing.

SUMMARY OF THE INVENTION

The aim of the invention is achieved with a method of processing of multichannel broad-band ultra-high-frequency electrocardiogram, which comprises the following steps:

providing an electrocardiogram comprising signals in at least two channels;

selecting at least two frequency ranges of the signal in each of the said at least two channels;

calculating an envelope for the signal in each frequency range in each channel;

dividing the calculated envelope of the signal in each frequency range in each channel into QRS complex segment envelopes;

computing an average or median envelope as an average or mean of all QRS complex segment envelopes for each frequency range in each channel;

optionally performing baseline correction for each average or median envelope by subtracting mean or median value from an interval in which QRS complex is not present (i.e., interval between QRS complexes) to remove noise background, normalizing the average or median envelope to obtain a normalized average or median envelope for each frequency range in each channel; wherein the normalization is performed by dividing the average or median envelope of each frequency range in each channel by its integral or by a maximal value reached in the average or median envelope, in each frequency range and each channel separately, wherein the integral or the maximal value are calculated within an interval of a minimum of 50 ms before the position of QRS complex and minimum 50 ms after the position of QRS complex;

calculating a signal average or median envelope from the normalized average or median envelopes of all frequency ranges within each channel; and calculating a first temporal duration of the signal average or median envelope as time length of a horizontal line crossing the signal average or median envelope, wherein the horizontal line is at a level corresponding to 10-70 percent of the maximum value of the signal average or median envelope; and/or calculating a second temporal duration of the signal average or median envelope as time difference between the first and the last intersection of the signal average or median envelope, wherein the horizontal line is at a level corresponding to 10-70 percent of the maximum value of the signal average or median envelope or of the final average or median envelope;

determination of the local depolarization duration of heart ventricles in units of time as the first temporal duration, and/or determination the total local depolarization duration of heart ventricles in units of time as the second temporal duration.

In some preferred embodiments, the method may further comprise the step of calculating a final average or median envelope from all signal average or median envelopes of the said at least two channels.

First temporal duration of the signal average or median envelope is designated herein as Vdi. Second temporal duration of the signal average or median envelope is designated herein as AVdi.

The Vdi and AVdi define the local depolarization duration of heart ventricles in units of time. Vdi and AVdi have different values when application of the threshold level (horizontal line) generates two or more peaks. Vd or AVd parameters may be calculated as mean or median value from Vdi or AVdi from the channels. The Vd or AVd parameters express the average depolarization activation time.

In one preferred embodiment, the method comprises further calculating a standard deviation of AVdi or Vdi values from the channels—the standard deviation is designated herein as SDVd. The SDVd expresses variability of local depolarization activation duration. A higher SDVd parameter indicates the simultaneous occurrence of fast and slow depolarization speed areas.

The method of the present invention may preferably further include the step of calculating a volumetric activation index (AIi) as an area delimited by the signal average or median envelope and horizontal line, wherein the horizontal line is at a level corresponding to 10-70 percent of the maximum value of the signal average or median envelope or a final average or median envelope, wherein the value of the signal average or median envelope or a final average or median envelope is normalized to 0 at the threshold level and 1 at the maximum level. This step may, for example, follow the steps of calculating the Vdi and AVdi.

The volumetric activation index of the signal average or median envelope is designated herein as AIi. The AIi defines the area delimited by the signal average or median envelope and threshold level (horizontal line), wherein the value of the signal average or median envelope is normalized to 0 at the threshold level and 1 at the maximum value level. AIi provides information corresponding to the number of simultaneously activated myocardial cells in a local volume.

The AI parameter expresses the average activation index. AI is calculated as the mean or median value from AIi from at least two channels.

Furthermore, a standard deviation SDAI is a standard deviation of AIi values from at least two channels, wherein the SDAI expresses the variability of local depolarization activation volume.

In one preferred embodiment of the invention, the signals are signals recorded in channels of V1, V2, V3, V4, V5, V6 electrocardiography leads or V1, V2, V3, V4, V5, V6, V7 and V8 electrocardiography leads.

In a preferred embodiment of the invention, a ventricular depolarization matrix is constructed so that each row of ventricular depolarization matrix is represented by a signal normalized average or median envelope for one of the said at least two ECG channels Minimal and maximal value in each row of ventricular depolarization matrix is detected, the minimal value is assigned to a first color, the maximal value is assigned to a second color. The values between minimum and maximum are assigned colors in the color range from the first color to the second color with linear or nonlinear color transition. Color representation of the ventricular depolarization matrix obtained using the assigned color forms a ventricular depolarization map (VDM). The ventricular depolarization map provides an image of the depolarization activity distribution over time and ventricular volume. From the ventricular depolarization map, the timing and duration of depolarizing activity in single ECG channel can be assessed easily. At the same time, it is possible to compare the timing of depolarization activity between individual channels.

In one preferred embodiment of the invention, the method further comprises a step of calculating an activation time (ATi) as time position of the center of mass of signal normalized average or median envelopes above the horizontal line crossing signal normalized average or median envelopes at 10-70 percent of the maximum of signal normalized average or median envelopes or time position of maximal value of signal normalized average or median envelopes, and subsequently calculating activation dyssynchrony (DYS) as time difference between activation times of two ECG channels. The DYS parameter indicates a time delay of ventricular depolarization between any two ECG channels. The relevant value is the highest value achieved for any combination of two channels used in the method of the invention.

In a preferred embodiment of the invention, the method further comprises a step of calculating relative activation dyssynchrony (RDYS) by dividing the activation dyssynchrony value DYS by Vd or AVd values. The RDYS parameter indicates the relationship between dyssynchrony and the speed of depolarization propagation. A higher RDYS value in patients prior to cardiac resynchronization device implantation indicates a potential positive response.

In one preferred embodiment of the invention, the method further comprises a step of calculating cumulative activation dyssynchrony and depolarization duration (PDYS) by adding the value of DYS and the value of Vd or AVd.

In one preferred embodiment of the invention, the method further comprises a step of calculating relative activation dyssynchrony variability SRDYS by dividing the dyssynchrony value DYS by the SDVd parameter. The SRDYS parameter indicates the relationship between dyssynchrony and the inter-lead variability of depolarization propagation speed.

The present invention further provides an apparatus for processing electrocardiographic signal. Said apparatus comprises:
one or more analogue amplifiers each including an input and an output, the input of each of the analogue amplifiers being connected to an output of a sensor of the ECG signal,
one or more analogue signal to digital signal converters each including an input and an output, the input of each of the analogue signal to digital signal converters being connected to the output of a corresponding one of the one or more analogue amplifiers,
wherein the sensors, the analogue amplifiers, and the analogue signal to digital signal converters have the transmission bandwidth at least 0.3 kHz, and
a processing unit including an input connected to the output of the analogue to digital signal converters and an output connected to at least one imaging unit, wherein the processing unit is configured to carry out the method of the present invention.

The imaging unit is preferably configured to display the VDM and/or more parameters selected from Vdi, AVdi, AIi, ATi, DYS, Vd, AVd, AI, SDVd, RDYS, PDYS and SRDYS.

Using the UHF-ECG processing apparatus and the method of processing the measured UHF-ECG signal, it is possible to diagnose various heart abnormalities and pathologies, which can be effectively treated by cardiac pacing. For successful cardiac pacing treatment, the time distribution of ventricular depolarization should be accurately identified. The present invention introduces a new technology for accurate determining of depolarization map that allows estimating new parameters for measuring the duration of depolarizing activity at the individual sites of the heart ventricles.

The invention thus further provides a method for finding an optimum placement of pacing lead or leads implant in a patient, comprising the steps of:
a) inserting pacing lead or leads tip in the heart ventricle or ventricles of a patient,
b) performing ventricular depolarization during pacing, and recording an electrocardiogram,
c) determining the values of DYS, Vdi, AVdi, AIi, Vd, AVd and AI parameters,
d) repeating the steps a) to c) in at least two different locations of insertion of pacing lead or leads tip, e) selecting the location with a minimal value of DYS, and optionally with minimum values of at least one of Vdi, AVdi, AIi, Vd, AVd, and AI parameters, f) finally implanting the pacing lead or leads on the location selected in step e).

The invention thus further provides a method for finding an optimal pacing device setting, comprising the steps of:

a) setting pacing device parameters, b) performing ventricular depolarization during pacing, and recording an electrocardiogram, c) determining the values of DYS, Vdi, AVdi, AIi, Vd, AVd and AI parameters, d) repeating the steps a) to c) at at least two different pacing device parameters settings, e) selecting the parameters setting with a minimal value of DYS, and optionally with minimum values of at least one of Vdi, AVdi, AIi, Vd, AVd and AI parameters, f) finally configuring the pacing device with parameters setting selected in step e).

Pacing device parameters include—voltage and pulse width, atrioventricular AV delay, interventricular VV delay and multi-site pacing electrode configuration.

Upper panel: VDM; Bottom panels: Vdi and AVdi parameters.

Figure 11:
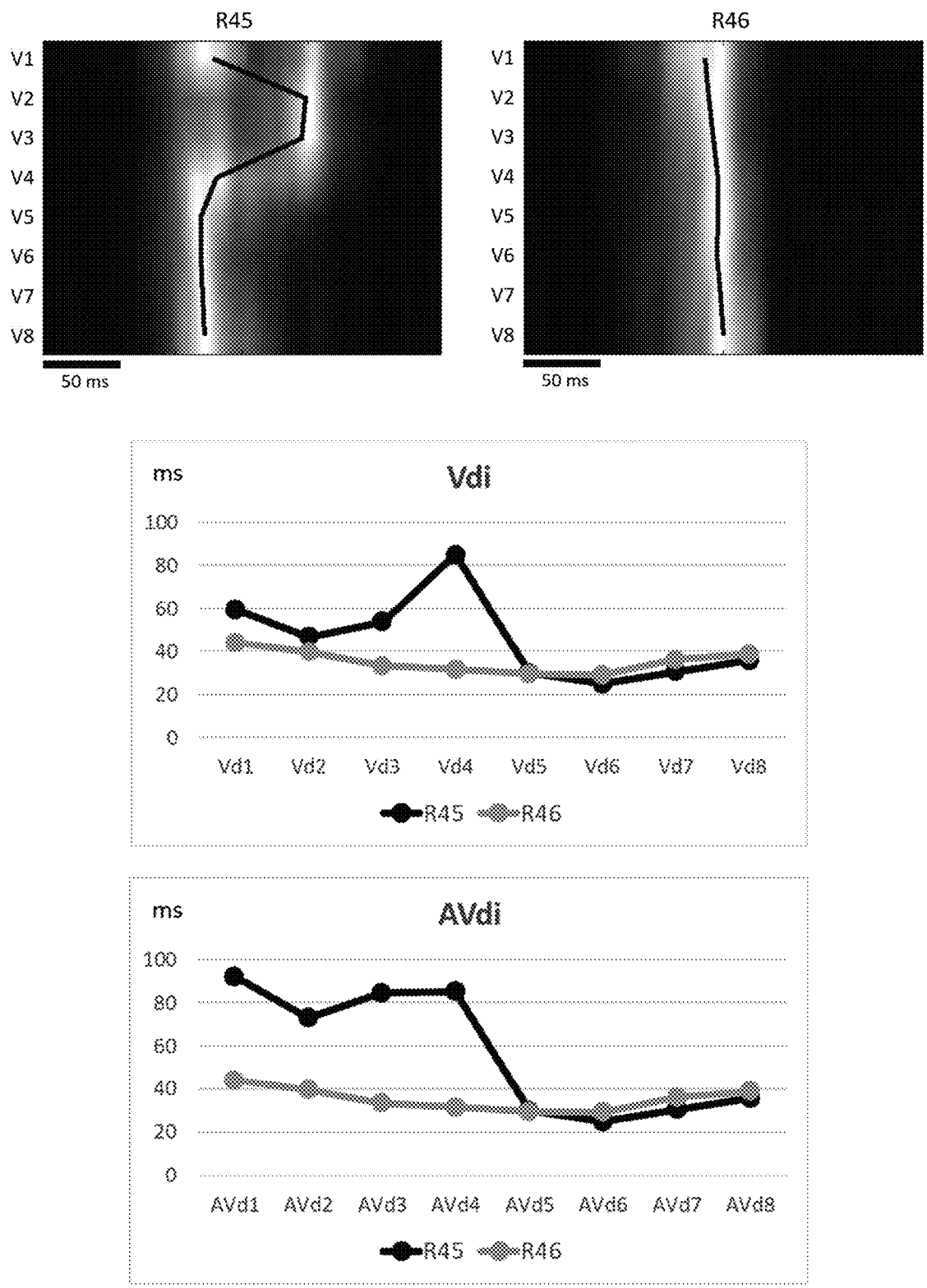

FIG. 11 Case 3: Right bundle branch block (RBBB) R45 and its correction by nonselective His bundle pacing R46, R45, DYS=64 ms, R46, DYS=11 ms.

Upper panel: VDM; Bottom panels: Vdi and AVdi parameters.

Figure 12:
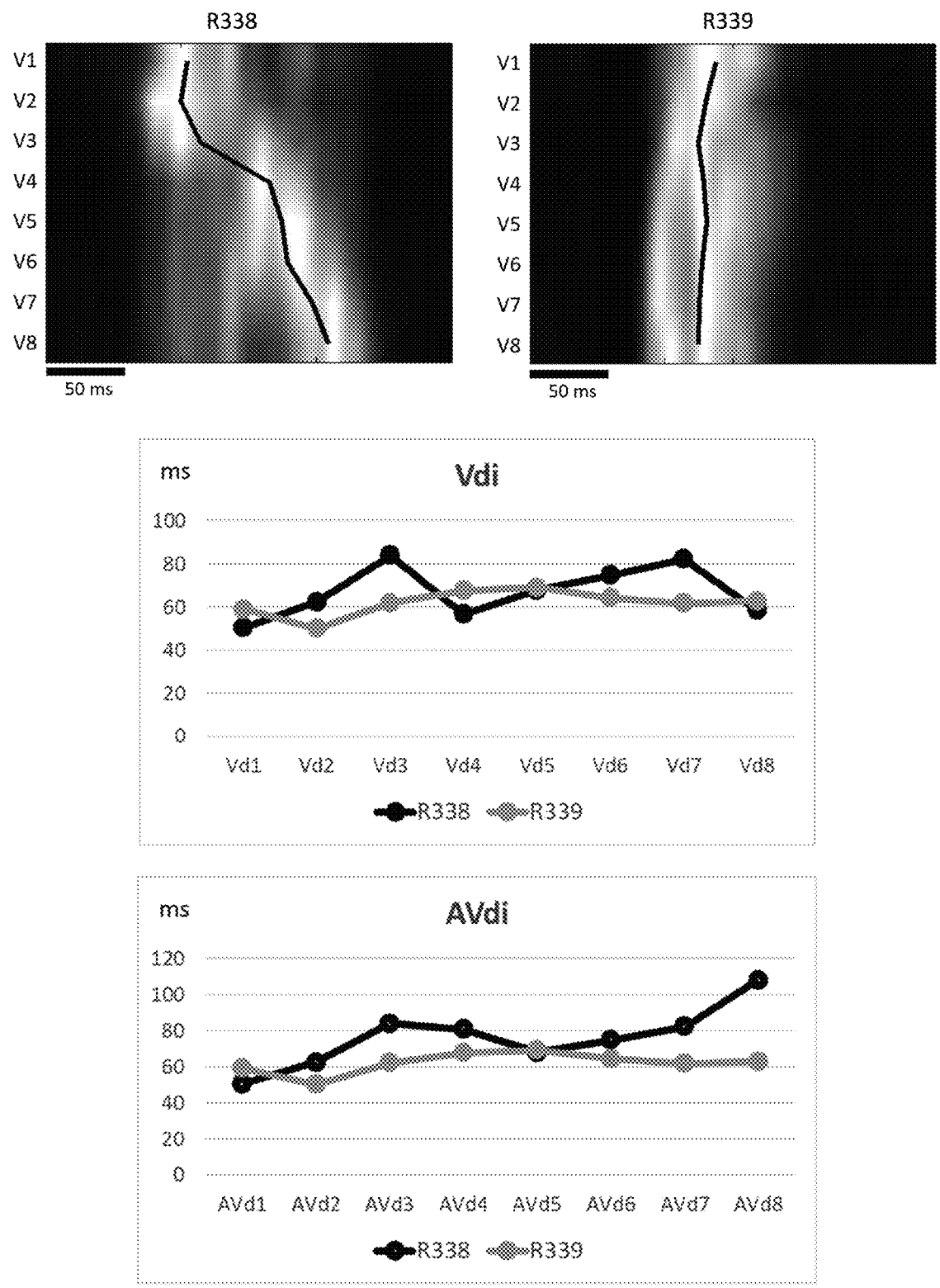

FIG. 12 Case 4: LBBB R338 correction by biventricular pacing R339, R338, DYS=87 ms, R339, DYS=11 ms.

Upper panel: VDM; Bottom panels: Vdi and AVdi parameters.

Figure 13:
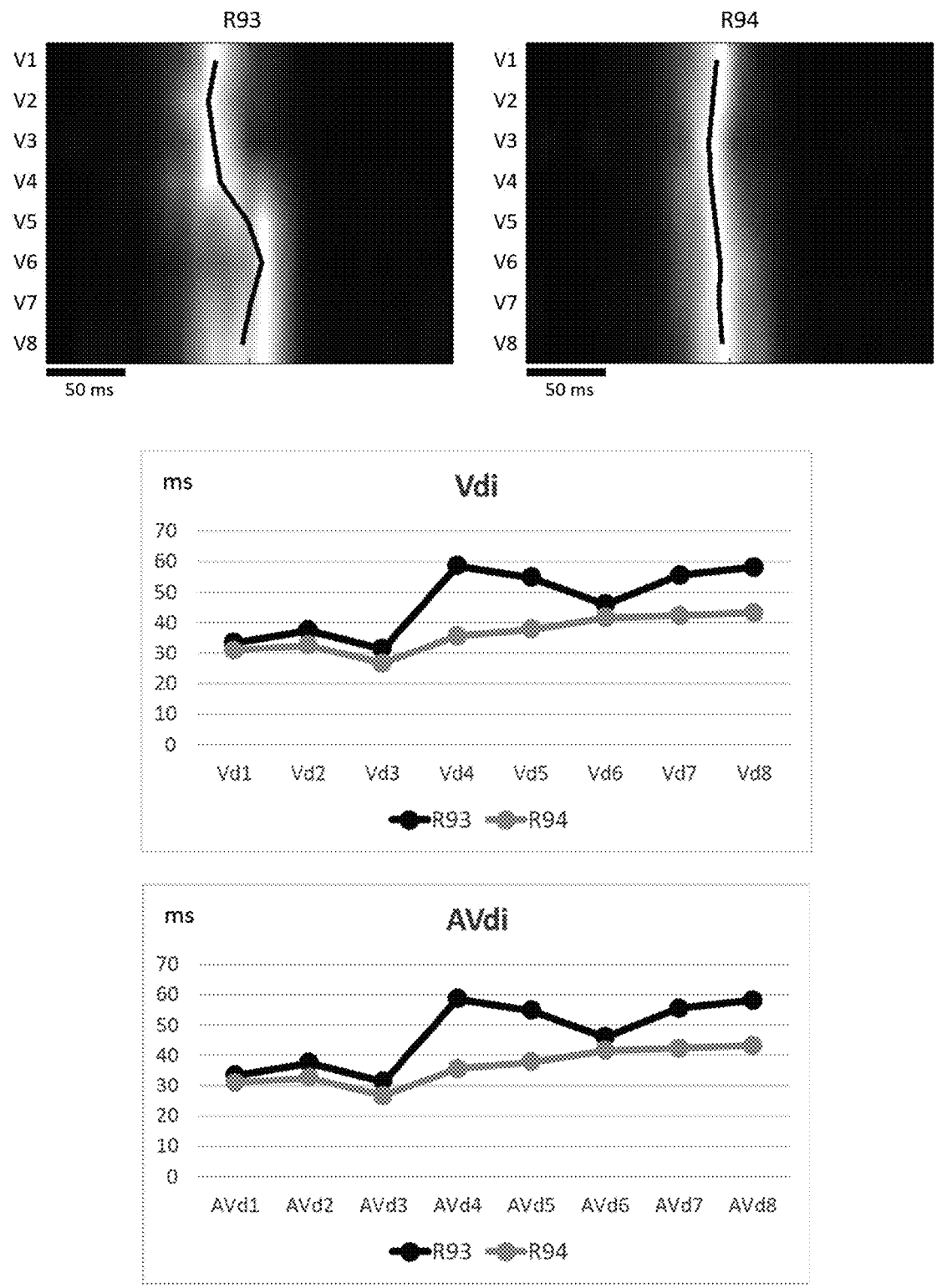

FIG. 13 Case 5: Pure myocardial capture of the septum R93, nonselective His bundle pacing R94, R93, DYS=31 ms, R94, DYS=8 ms.

Upper panel: VDM; Bottom panels: Vdi and AVdi parameters.

Figure 14:
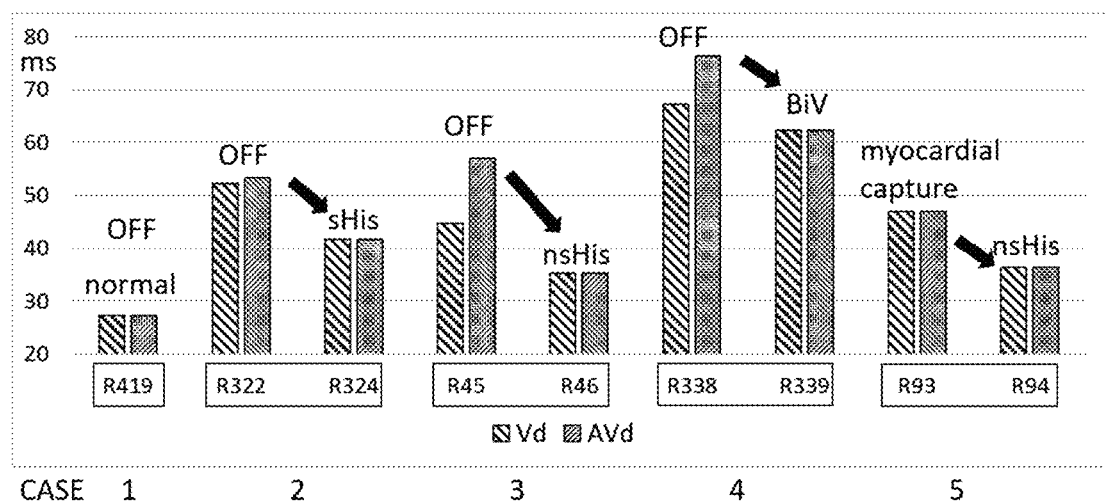

FIG. 14 Vd and AVd parameters for different records. Black arrows indicate the decrease of the Vd and AVd pacing OFF vs. pacing ON or between myocardial and nsHis pacing. The difference between Vd and AVd in record R45 indicates a double electrical activations in a single electrode (here V1-V3—see FIG. 11). sHis—selective His-bundle pacing, nsHis—nonselective His-bundle pacing, BiV—biventricular pacing.

Figure 15:
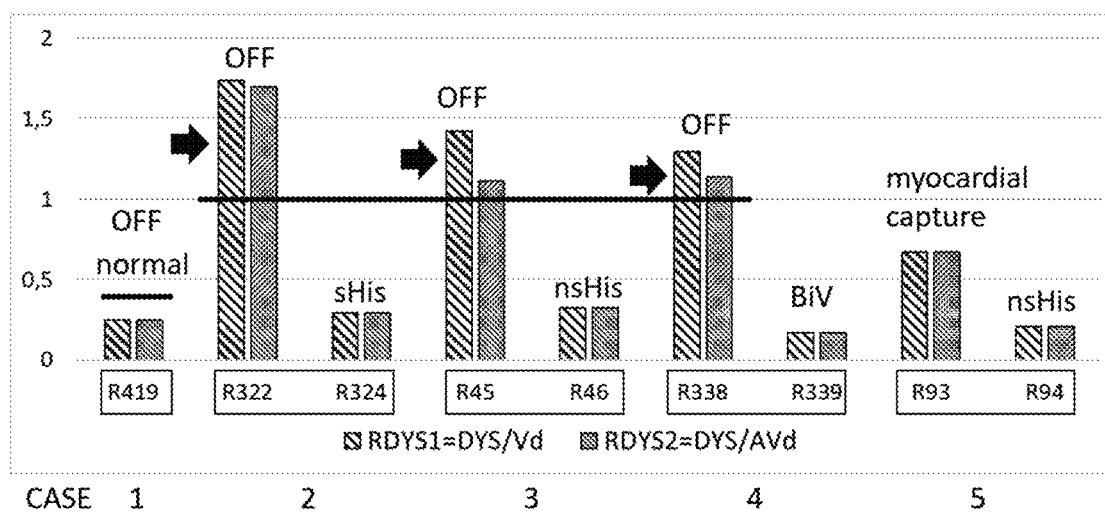

FIG. 15 RDYS parameter for different records. The RDYS parameter indicates the relationship between dyssynchrony DYS and the speed of depolarization propagation Vd or AVd. A higher RDYS value in patients before device implantation (OFF) can indicate a potential positive response (black arrows). sHis—selective His-bundle pacing, nsHis—nonselective His-bundle pacing, BiV—biventricular pacing.

Figure 16:
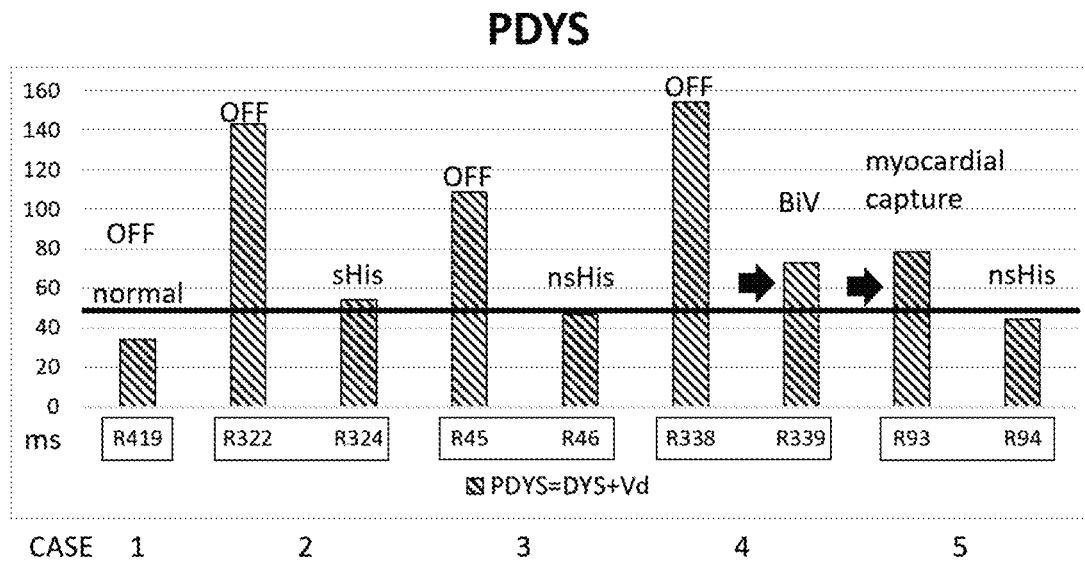

FIG. 16 PDYS parameter for different records. The PDYS parameter indicates the sum of dyssynchrony DYS and a mean or median speed of depolarization propagation Vd or AVd. A higher PDYS value in patients during pacing can indicate a potential less positive or negative response (black arrows). sHis—selective His-bundle pacing, nsHis—nonselective His-bundle pacing, BiV—biventricular pacing.

Figure 17:
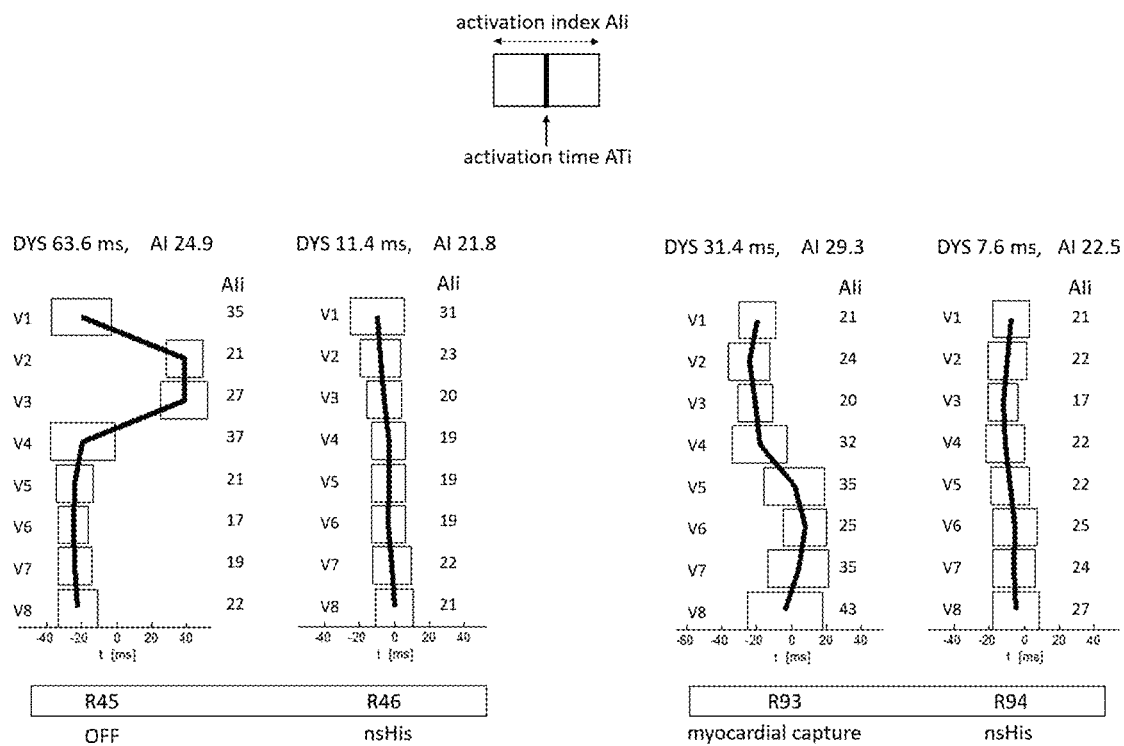

FIG. 17 Case 6: AT, ATi, AI, and AIi parameters for R46, R46, R93, and R94 records. The activation times ATi indicates the time position of the myocardial cells activation in the region near Vi lead. AT parameter is mean from ATi parameters. The activation index AIi is the value, which corresponds to the duration and volume of simultaneously activated myocardial cells in the region near Vi lead. AI parameter is mean from AIi parameters. Straightening the ATi vertical line implies a reduction in dyssynchrony DYS; shortening the rectangles AIi means a local activation acceleration. nsHis—nonselective His-bundle pacing.

Figure 18:
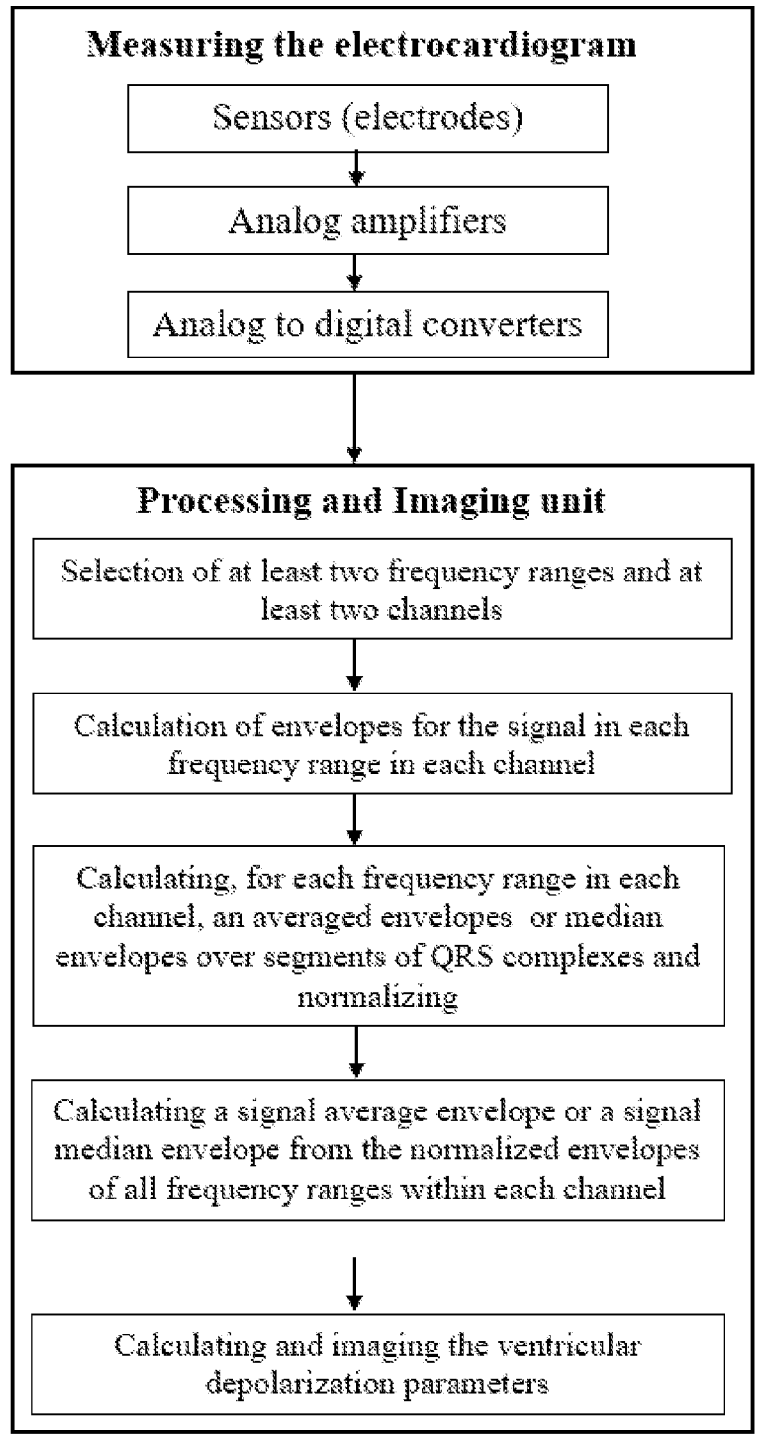

FIG. 18 is a schematic representation of the system for the method of the invention.

DETAILED DESCRIPTION OF THE INVENTION

The invention will be further illustrated using exemplary embodiments, and with reference to the figures.

Object of the invention is a method of processing of multichannel broad-band ultra-high-frequency electrocardiogram.

The broad-band ultra-high-frequency electrocardiogram is a plurality of signals recorded by a plurality of measurement electrodes and presented as a plurality of signals in channels. The signals are measured in a frequency range above 100 Hz. Currently, the signals are typically measured in frequency ranges starting from 100 Hz and up to 1000 Hz, but any measuring frequency range is compliant with the present invention.

Typically, 2 to 256 channels are used. Signals from the leads V1-V6 or V1-V8 are preferred for this invention. The signals are a dependency of electrical potential (voltage) and time.

The method processes electrocardiogram comprising signals from at least two channels. Signals from the leads V1-V6 or V1-V8 are preferred. Signals from all channels, or signals only from some channels can be used in the method of the invention.

Preferably, the electrocardiogram is digitized. For example, the parameters of the digitizer may be 24 bits word length and a sampling rate of 5 kHz. Other digitization parameters may be used, as known to the person skilled in the art.

The signal in each channel is recorded in a total frequency range of above 100 Hz, preferably 100 to 1000 Hz, and can be divided into several frequency ranges.

In the following text, the channels will be designated as "CHi" which means "the i-th channel". The frequency ranges will be designated as "Fj" which means "the j-th frequency range". "CHiFj" means "the j-th frequency range in the i-th channel".

At least two frequency ranges are selected in each of the said at least two channels. The frequency ranges are frequency bands above the frequency of 100 Hz. Width of each frequency range may preferably be from 50 to 400 Hz. The frequency ranges are preferably the same in each channel.

An envelope (EnvCHiFj) of the signal is calculated for each frequency range in each channel.

An envelope is a smooth curve outlining the extremes of the oscillating signal. In this invention, the upper envelope is considered as envelope, i.e., the curve outlining the upper extremes of the signal.

The envelope may be an amplitude envelope or a power envelope. The amplitude envelope is an envelope outlining the amplitude extremes of the signal. The power envelope is an envelope outlining the power extremes of the signal (power=amplitude squared).

In preferred embodiments, the amplitude or power envelopes of the ECG channel are calculated using Hilbert transformation, or the amplitude envelopes of the ECG channel are calculated by filtration, conversion of the signal obtained in this way into an absolute value and smoothing it, or the power envelopes of the ECG channel are calculated by filtration, raising the ECG signal to the power of two and smoothing it.

The calculated envelope of the signal in each frequency range in each channel into QRS complex segment envelopes, wherein a QRS complex segment envelope is a portion of the envelope of the signal, said portion corresponding to one QRS complex, i.e., outlining one QRS complex.

Figure 1:
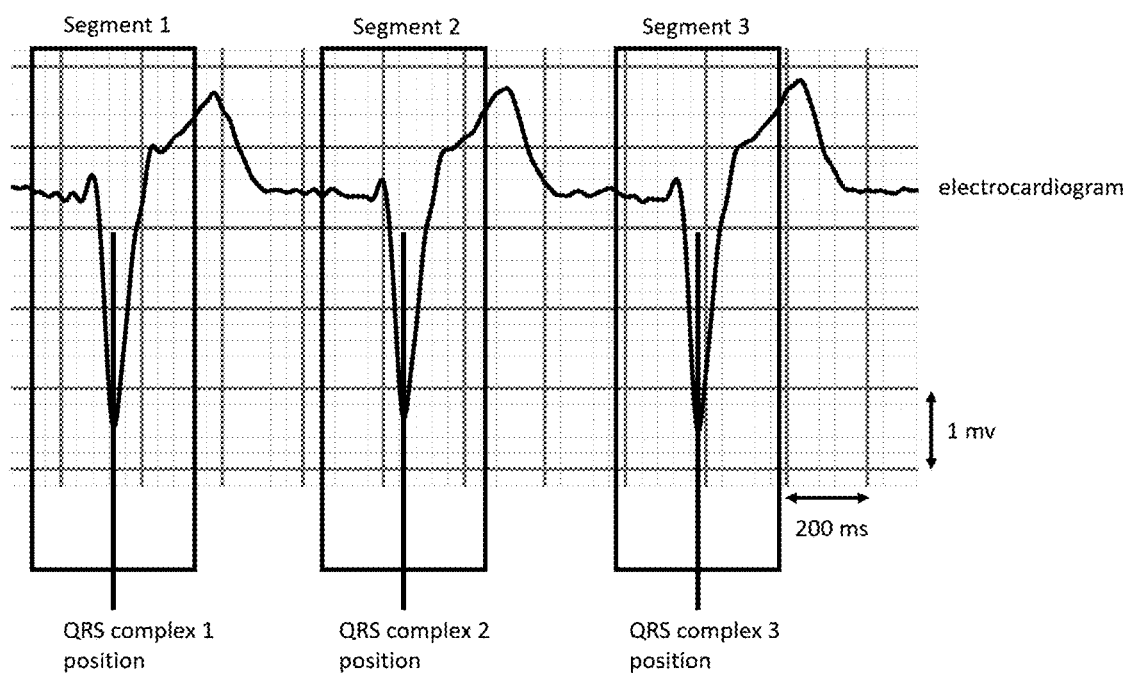
FIG. 1 generally shows QRS complex segments, and positions of QRS complexes in an electrocardiogram. QRS complex position=temporal position of QRS complex. QRS complex segment=a period of time comprising the entire QRS complex.
Figure 2:
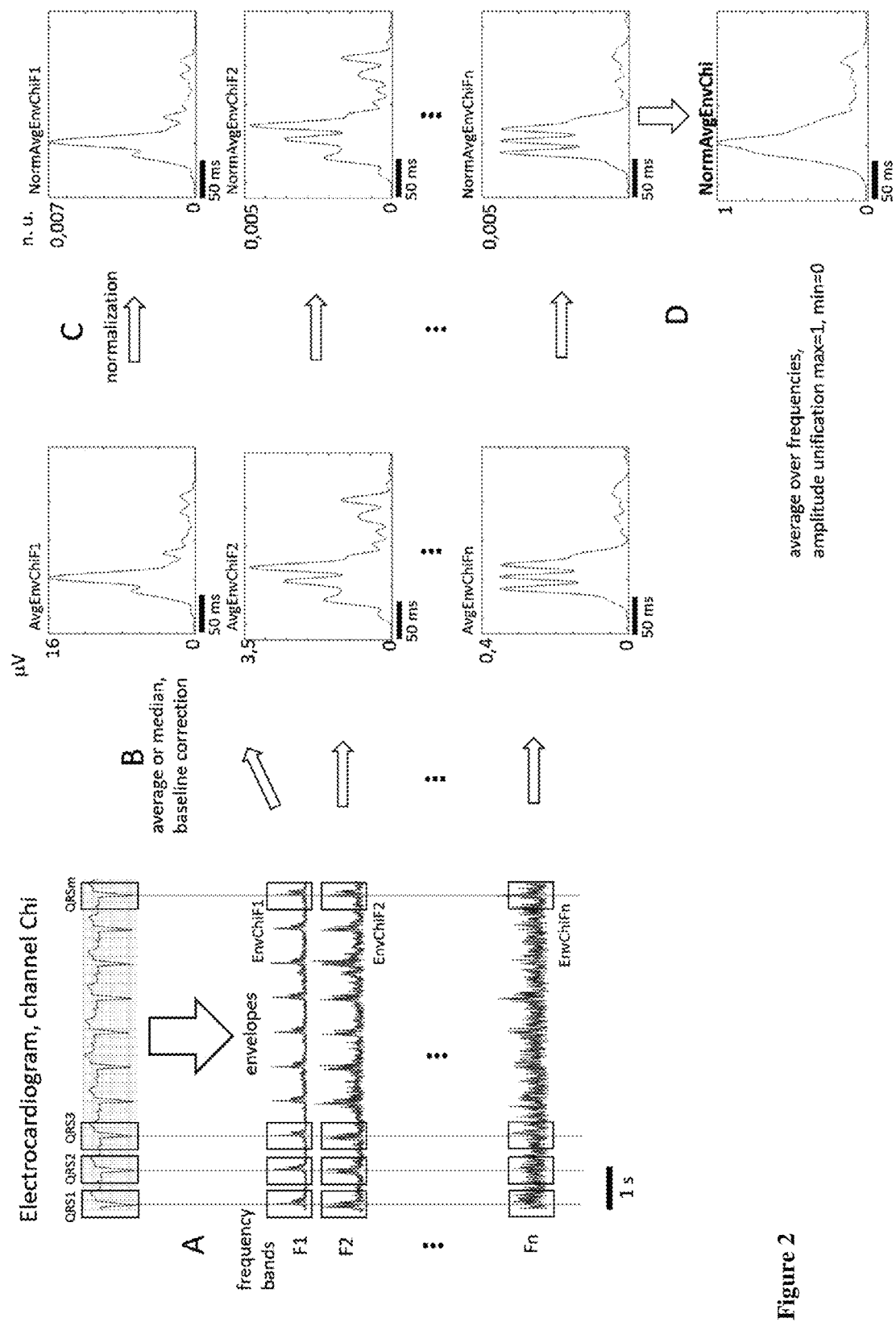
FIG. 2 schematically shows the electrocardiographic signal in one channel, calculation of envelopes, averaging and normalization.
- A—amplitude or power envelopes in two or more frequency bands above 100 Hz,
- B—the average or median of amplitude envelopes in ECG channel Chi and frequency band Fj—AvgEnvChiFj, the baseline correction,
- C—the normalized AvgEnvChiFj, normalization is provided by dividing AvgEnvChiFj by integral of AvgEnvChiFj or maximal value of AvgEnvChiFj, in each frequency range and selected ECG channel separately—NormAvgEnvChiFj. NormAvgEnvChiFj in the figure was acquired by integral normalization,
- D—average amplitude or power envelope over all frequency bands in single ECG channel Chi—NormAvgEnvChi. NormAvgEnvChi amplitude unification, maximal value=1, minimal value=0.

QRS complex segment envelope is preferably a portion of the envelope of the signal which starts at least 50 ms, or 50 to 500 ms, or 50 to 150 ms, or 120 to 200 ms before the position of the QRS complex, and ends at least 50 ms, or 50 to 500 ms, or 50 to 150 ms, or 120 to 200 ms after the position of the QRS complex. The position of the QRS complex is the temporal center of the QRS complex. The position of QRS complex can be detected by algorithms known to the person skilled in the art. An example of the position of the QRS complex and of QRS complex segment is shown in FIG. 1 and FIG. 2A.

An average or median envelope (AvgEnvCHiFj) is then computed from the QRS complex segment envelopes within each of the frequency ranges, in each of the channels. This step increases a signal-to-noise ratio for each frequency range in each channel (FIG. 2B).

Baseline correction may optionally be performed for each average or median envelope by subtracting mean (average) or median value from a temporal interval in which QRS complex is not present to remove noise background. Baseline correction is particularly useful if in the following step of normalization, integral is used.

The average or median envelope are normalized to obtain a normalized average or median envelope (NormAvgEnvCHiFj) for each frequency range of the signal from each channel. The normalization is performed by dividing the average or median envelope of each frequency range of the signal from each channel by its integral or by a maximal value reached in the average or median envelope. The integral or the maximal value are calculated within an interval of minimum of 50 ms before the position of QRS complex and minimum of 50 ms after the position of QRS complex. One normalized average or median envelope (NormAvgEnvCHiFj) is obtained for each frequency range in each channel (FIG. 2C).

Calculations of average, median or normalization are performed in the sequence of points whose time distance from the QRS complex is equal. In other words, each point (e.g., sampling point) of the average, median or normalized envelope is calculated as an average, median or normalized value, respectively, of the points in the same temporal position of all envelopes over which the calculation of the average, median or normalization is performed.

Signal average or median envelope (NormAvgEnvCHi) is calculated from the normalized average or median envelopes of all frequency ranges within each channel. The calculation is performed by averaging or determining median of normalized average or median envelopes from all frequency ranges from the channel CHi. This calculation is performed in each channel, and one signal average or median envelope is obtained for one channel (FIG. 2D).

Figure 4:
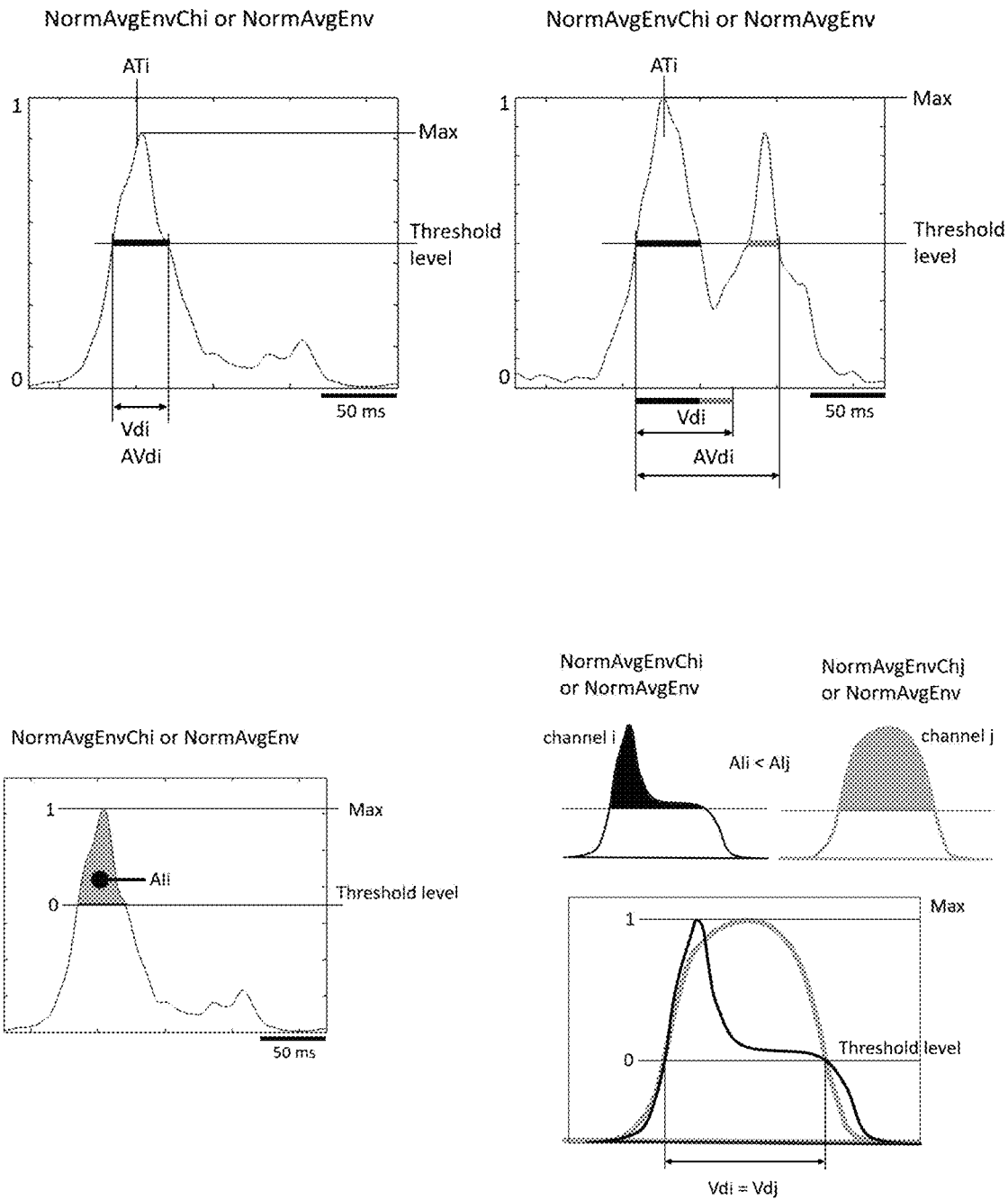
FIG. 4 ATi, Vdi, AVdi, and AIi numerical parameters computation. Upper panel:
- ATi—local activation time—position of center of gravity (left panel) or maximal value (right panel) of NormAvgEnvChi or NormAvgEnv above a threshold.
- Max—maximum of NormAvgEnvChi or NormAvgEnv
- Threshold level—selected thresholds related to maximum Bottom panel:
- AIi—activation index computed as integral of NormAvgEnvChi or NormAvgEnv above a threshold—gray or black areas.
Figure 5:
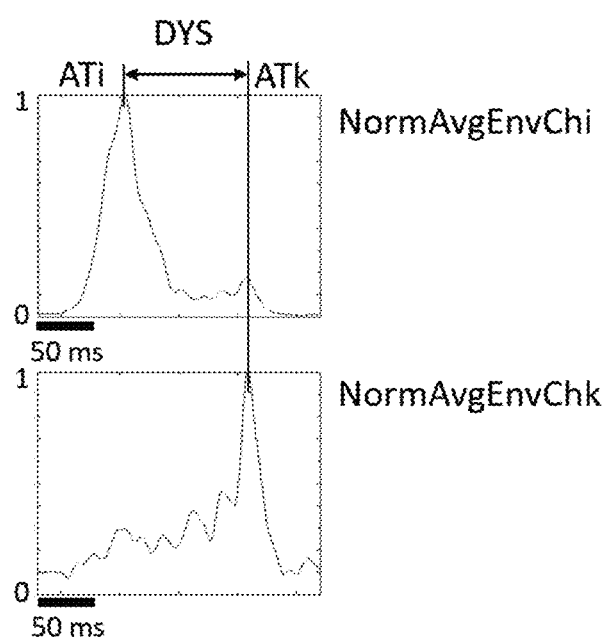
FIG. 5 DYS numerical parameter computation as time difference between two activation times ATi and ATk. ATi and ATk—local activation times in ECG channels i and k.
Figure 6:
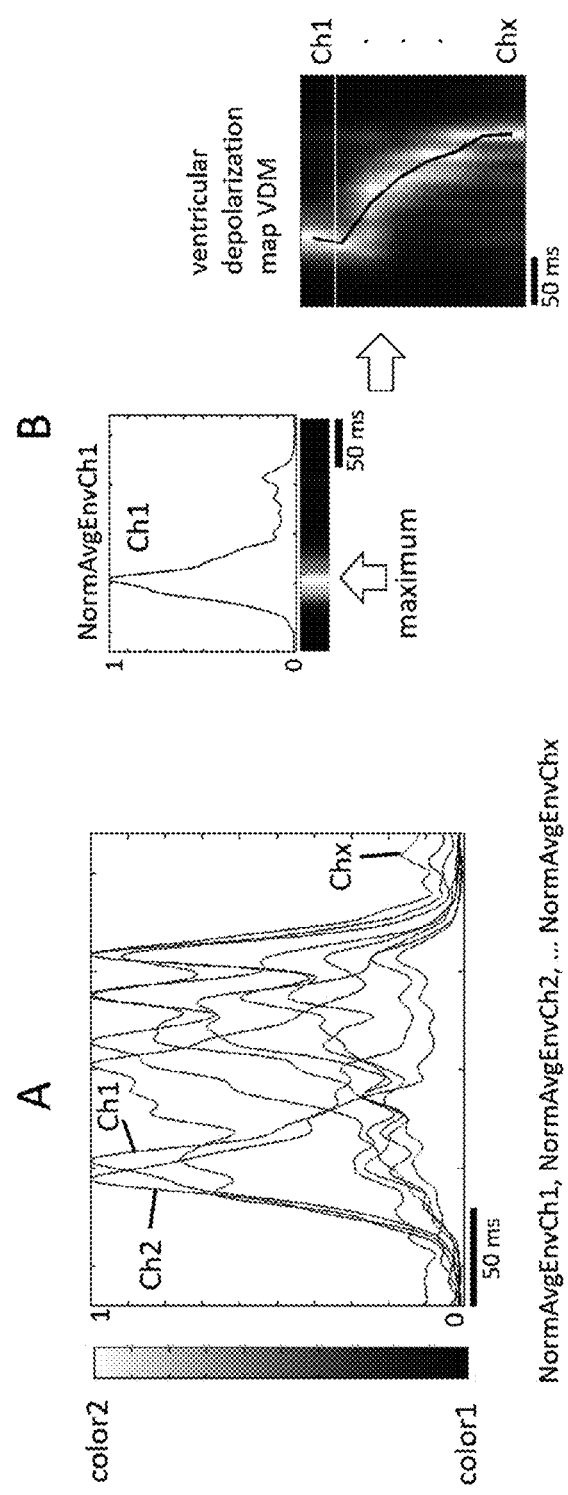
FIG. 6 Ventricular depolarization map VDM
- A—NormAvgEnvChi, maximal value in each NormAvgEnvChi=1, minimal value in each NormAvgEnvChi=0, the minimal value is assigned to color1, the maximal value is assigned to color2.
- B—Ventricular depolarization map VDM. Each horizontal row of the map represents the NormAvgEnvChi for single ECG channel Chi, the maximal amplitude in each row is represented in color1 and the minimal in color2.
Figure 7:
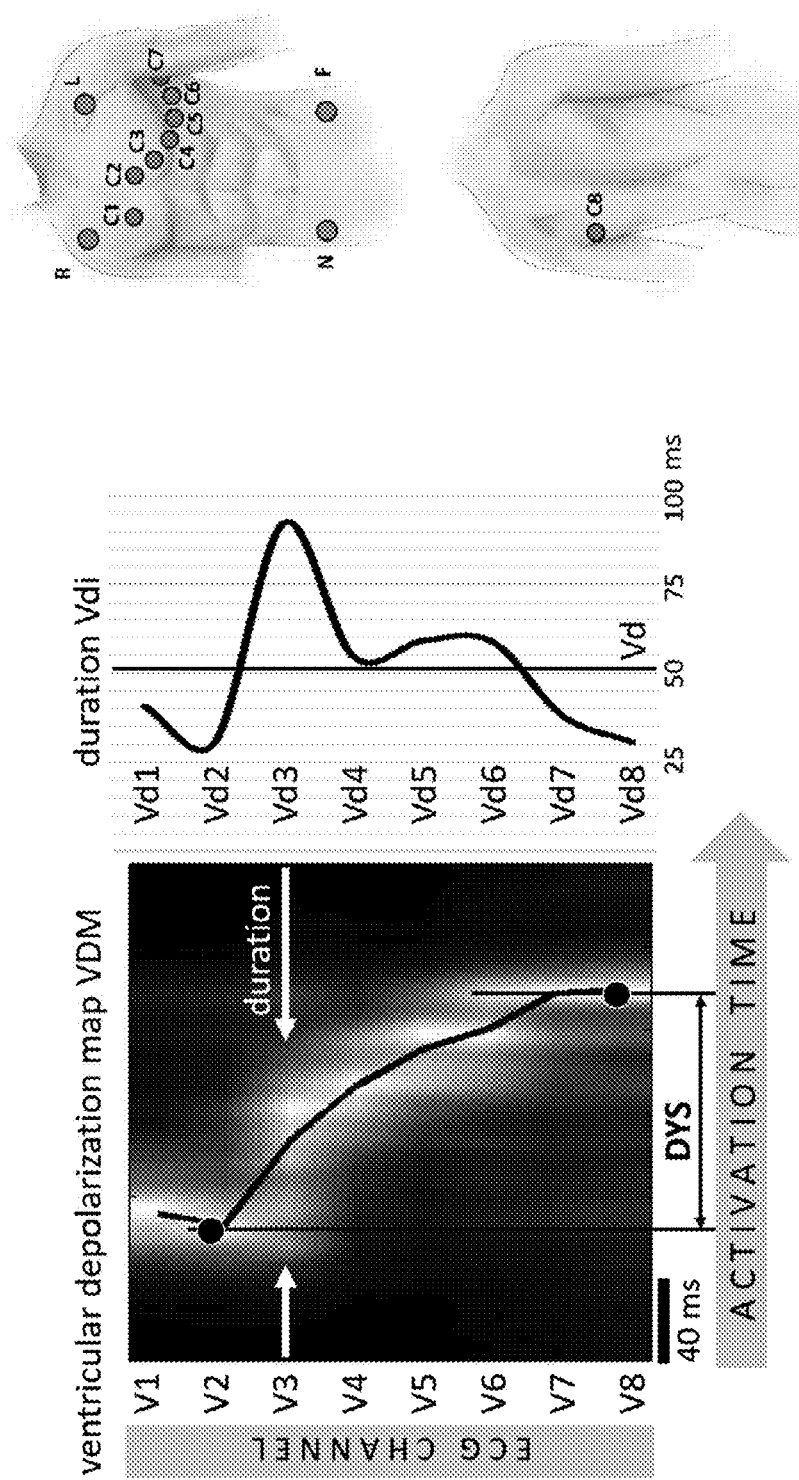
FIG. 7 Interpretation of VDM and Vdi, 14-lead broadband ECG, V1-V8 precordial ECG leads. Colors (or shades of grey, here) indicate time (horizontal axis) and spatial (vertical axis) depolarization distribution. DYS is here determined as the distance between the first (lead V2) and the last (lead V8) local activation times. The local activation duration (Vdi) is determined here as the duration of depolarization activity in single lead in the 50 percent of the maximum. High Vdi values point to an area of slow conduction. Vd represents mean from all Vdis.

First temporal duration (Vdi) of the signal average or median envelope is calculated as time length of a horizontal line crossing the signal average or median envelope with a horizontal line at a level corresponding to 10-70 percent, preferably 30-60 percent, more preferably 40 to 50 percent, of the maximum value of the signal average or median envelope (FIG. 4).

The time length is calculated as distance in units of time from the first intersection of the NormAvgEnvCHi with the horizontal line at the corresponding level to the second intersection of the NormAvgEnvCHi with the horizontal line at the corresponding level. Depending on the selected level, a third and fourth intersection of the NormAvgEnvCHi with the horizontal line at the corresponding level may occur, and then the distance between the third and fourth intersection is added to the distance between the first and second intersection.

Second temporal duration (AVdi) of the signal average or median envelope (NormAvgEnvCHi) is calculated as time difference between the first and the last crossing of the signal average or median envelope with a horizontal line at a level corresponding to 10-70, preferably 30-60 percent, more preferably 40 to 50 percent, percent of the maximum of the signal average or median envelope (FIG. 4).

The time length is calculated as distance in units of time from the first intersection of the NormAvgEnvCHi with the horizontal line at the corresponding level to the last intersection of the NormAvgEnvCHi with the horizontal line at the corresponding level.

Figure 3:
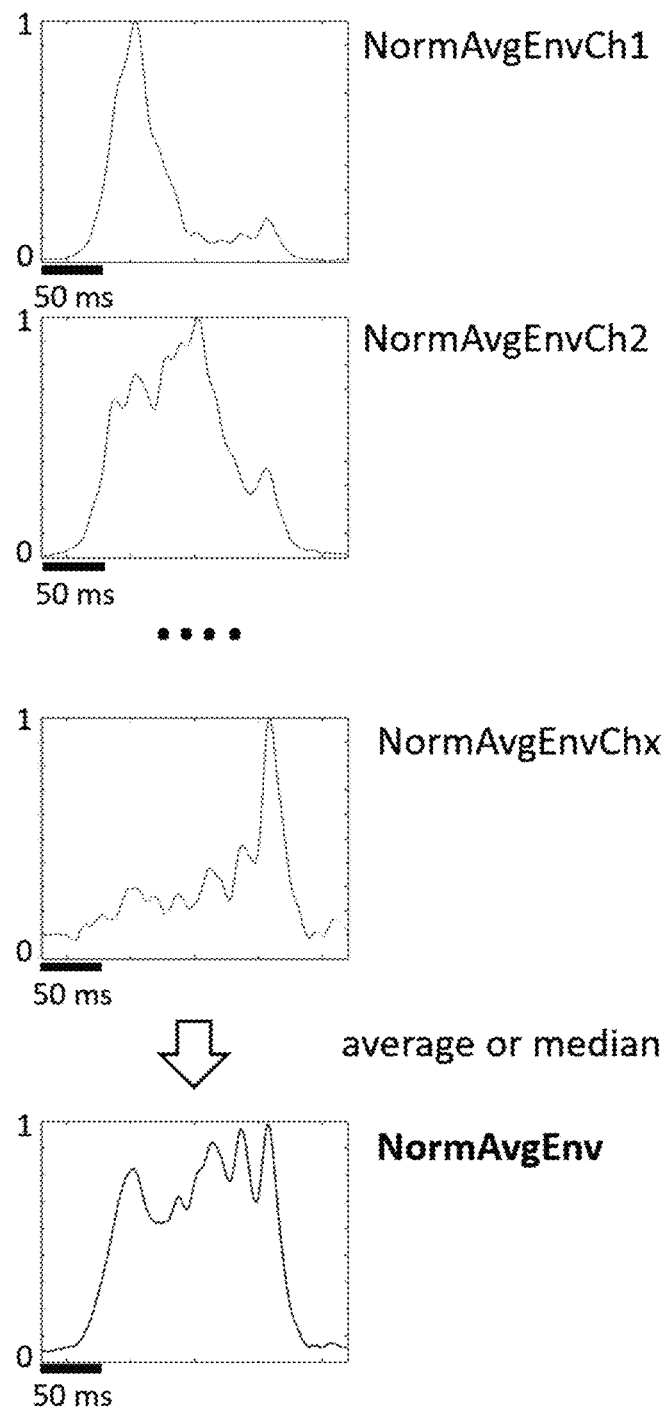
FIG. 3 NormAvgEnv is calculated as an average or median from NormAvgEnvChi from selected ECG channels (Ch1, Ch2, . . . , Chx).

Optionally, a final average or median envelope (NormAvgEnv) is calculated as an average or median from all signal average or median envelopes (NormAvgEnvCHi) (FIG. 3).

Finally, local depolarization duration of heart ventricles is determined in units of time as the first temporal duration, and/or determination the total local depolarization duration of heart ventricles in units of time as the second temporal duration.

The main field of application of the invention is cardiac pacing. Cardiac pacing has been the standard treatment for severe bradyarrhythmia for decades. It is a reliable, proven method with a generally low incidence of complications. It relies on the stimulation of the heart chambers of patients via electrodes connected to the implantable pulse generator (IPG). The electrical pulse generated in the IPG is delivered to the heart through the leads and activates myocardial cells to provide electromechanical interaction with resulting myocardial contraction.

Direct pacing of the myocardium of heart ventricles is a clinically preferred method of cardiac pacing. In this situation, electrical pulse causes excitement of myocardial cells in close relation to the lead tip and incurred electrical activity is spreading as an electrical wave-front to adjacent regions of heart ventricles. Contrary to the physiological situation, where the electrical impulse is spreading fast through the conductive system (2-4 m/s) and results in synchronous ventricular activation/contraction, trans-myocardial cell to cell conduction can be more than ten times slower (0.15-0.40 m/s). It is resulting in slow electrical wave-front propagation in ventricular myocardium and delayed activation of distant regions related to the site of pacing. In many patients, single-chamber stimulation can result in electromechanical dyssynchrony of heart ventricles with resulting heart failure.

Biventricular pacing was developed as a method of electrical resynchronization of heart ventricles in patients with their dyssynchrony due to bundle branch block. It showed to improve the cardiac output by resynchronization of ventricular electromechanical activity and to improve outcome in patients with heart failure. Although an overwhelming number of procedures were performed worldwide since the method was introduced, the fact is that a significant portion of patients does not positively respond to the therapy. One of the reasons is the imperfect electrical resynchronization provided by biventricular pacing as it relays on myocardial pacing from the right and left ventricle. Slower depolarization of ventricular myocytes is aggravated by non-physiological electrical wave-front propagation (epi-endo direction) caused by pacing from the left ventricular lead placed in the branch of coronary sinus.

In recent years, new techniques of permanent cardiac pacing were introduced. They are His bundle, left bundle branch, and left ventricular septal pacing—all together can be designated as conductive system pacing techniques. They offer more physiological ventricular activation as they primarily activate parts of the conductive system, and, as such, they provide fast myocardial depolarization.

Clinical applications of the broad-band UHF-ECG signal processing with a focus on the parameters of the speed of myocardial depolarization—Vdi, AVdi, Vd and AVd—are introduced within the framework of the present invention.

Vdi, AVdi, and AIi parameters provide essential information about the speed of the myocardial depolarization in the myocytes adjacent to the specific lead. As shown below, it is different in healthy patients compared to patients with the conduction problem in the left or right Tawara branch, and also it is different during different types of ventricular pacing (myocardial vs. conductive system vs. epicardial pacing). Such information cannot be obtained from the 12-lead ECG and QRS complex duration.

Vd or AVd parameters are calculated as a mean or median value from Vdi or AVdi from selected ECG channels. The Vdi and AVdi parameters are the same if the selected threshold line passes through the NormAvgEnvCHi without interruption (FIG. 4, upper left panel). If there are separate peaks in NormAvgEnvCHi, the threshold line is interrupted (FIG. 4, upper right panel). In that case, the Vdi and AVdi parameters have a different value. This difference is also reflected in Vd and AVd parameters. Different values of Vd and AVd indicate the existence of multiple activations in one or more ECG leads related to right ventricle free wall and septal different activation (FIG. 14).

The AIi is calculated as an area delimited by the signal average or median envelope and threshold, wherein the value of the signal average or median envelope or a final average or median envelope is normalized to 0 at the threshold level and 1 at the maximum level (FIG. 4). Thus, the AIi parameter is less sensitive to noise and artifacts than Vdi and AVdi parameters. Signal average or median envelope values that only slightly exceed the threshold have little effect on the AIi value. AIi is less sensitive to changes but more robust.

Figure 8:
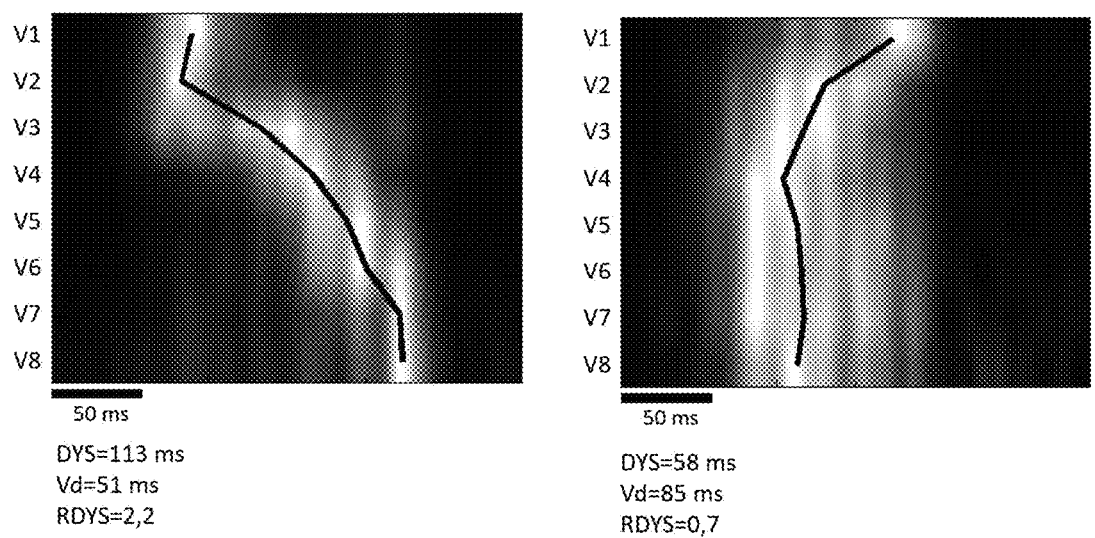
FIG. 8 Example of different RDYS parameters. RDYS=DYS/Vd. A higher RDYS value reflects the higher dyssynchrony simultaneously with a fast local conduction.

RDYS parameter is calculated as a division of dyssynchrony value DYS by Vd or AVd parameters (FIG. 8). High RDYS value especially in records before pacing device implantation or during pacing device switched off indicates a potential positive response to resynchronization (FIG. 15). PDYS parameter is calculated so that the value of DYS is added to the value of Vd or AVd. High PDYS value in patients especially during cardiac resynchronization therapy indicates a potential less positive or even negative resynchronization response (FIG. 16).

EXAMPLES

The examples of clinical application given in this text are based on the following ECG recording and processing configuration:

ECG signal was recorded with sampling frequency 5 kHz and dynamic range of 26 bits (3 nV resolution) and a frequency range of 1.5 kHz. ECG data was collected over 0.5-5 minutes in a resting supine position with a standard 14-lead ECG setup. For each precordial lead (eight ECG channels V1-V8), the amplitude envelopes were computed in sixteen frequency bands F1-F16: 150-250, 200-300, 250-350, 300-400, 350-450, 400-500, 450-550, 500-600, 550-650, 600-700, 650-750, 700-800, 750-850, 800-900, 850-950, and 900-1000 Hz using the Hilbert transform. Amplitude envelopes EnvCHiFj were calculated and then segmented by R wave annotation (determination of QRS position) within the QRS complex to obtain QRS complex segment envelopes. In each frequency band Fj of each ECG channel CHi, the median amplitude envelopes were computed as the median value of the points of the QRS complex segment envelopes (AvgEnvCHiFj, FIG. 2). Baseline correction was performed. Baseline correction was computed by subtracting mean from an interval of 150-250 ms after the position of Ra from AvgEnvCHiFj. Thereafter, the median amplitude envelopes of each frequency band were normalized. Normalization was performed using the integral, which was calculated in the interval of 120 ms before the QRS position and 120 ms after the QRS position. Subsequently, all median envelope values were divided by this integral (NormAvgCHiFj). This procedure achieves that the integral in all frequency bands is the same. Normalization in the various frequency domains was used to avoid that the larger low-frequency amplitudes would dominate the weak high-frequency amplitudes during the subsequent averaging over frequencies.

Figure 9:
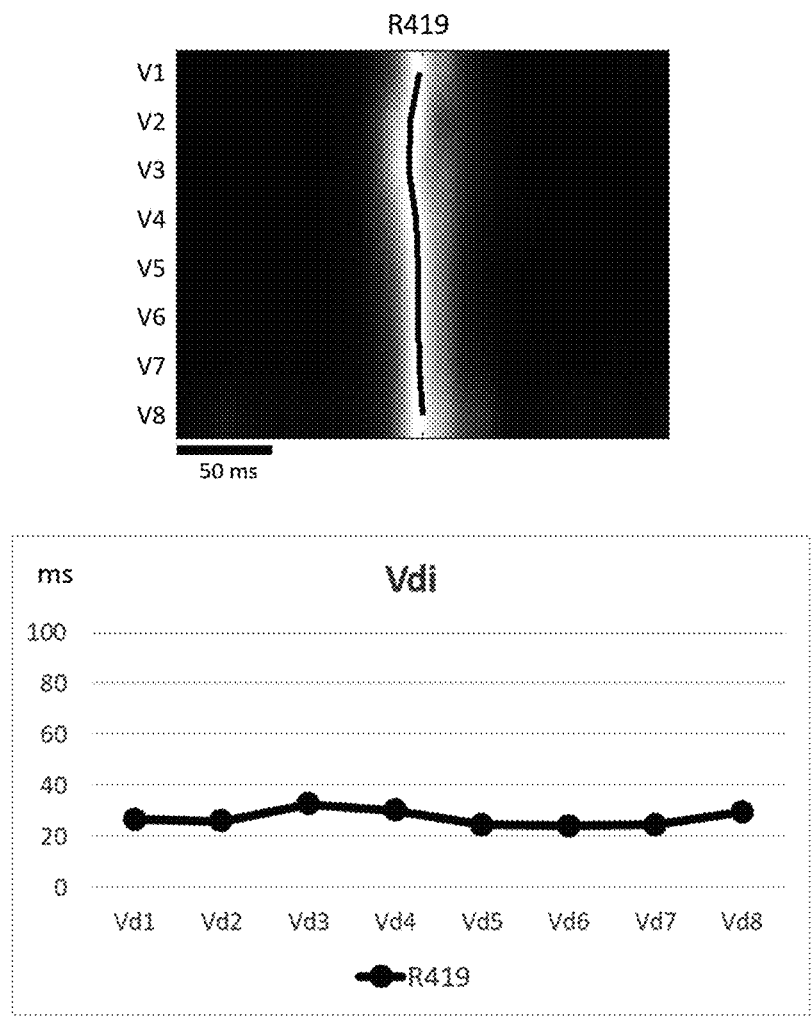
FIG. 9 Case 1: spontaneous rhythm with narrow QRS, R419, DYS=7 ms. Upper panel: VDM; Bottom panel: Vdi parameters.

The following examples show the relationship between these parameters during different types of pathologies and stimulations:

Case 1: Normal heart, spontaneous rhythm with narrow QRS, R419, FIG. 9.

An example of the ventricular depolarization map VDM in a healthy patient with a narrow QRS complex (QRS duration of 86 ms) without any obvious conduction problem in the ventricles on the 12-lead ECG is shown. Due to sudden activation of all ventricular myocardium without any apparent myocardial cell to cell conduction problem, Vd1-Vd8 parameters are short and do not exceed 33 ms, which means quick myocardial depolarization of all segments in both heart ventricles.

Figure 10:
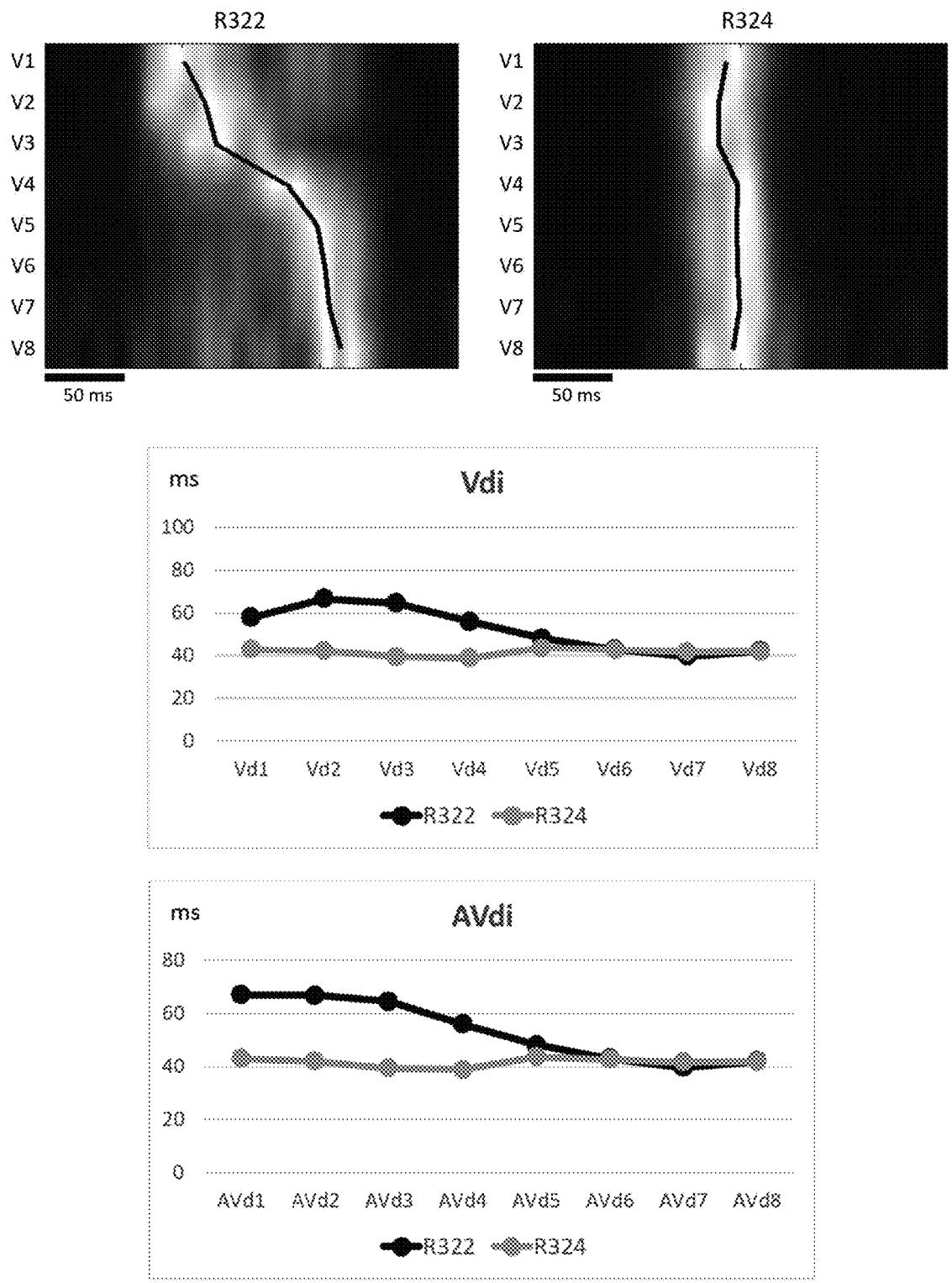
FIG. 10 Case 2: Left bundle branch block (LBBB) R322 and its correction by selective His bundle pacing R324, R322, DYS=91 ms, R324, DYS=13 ms.

Case 2: Left bundle branch block (LBBB) R322 and its correction by selective His bundle pacing R324, FIG. 10.

An example of the VDM of the patient with the conduction block in the left Tawara branch and its correction by His bundle pacing is shown. Due to the left bundle branch block, electrical wave-front spreads from the right ventricle through the interventricular septum by a slow trans-myocardial cell to cell conduction, and this results in deceleration of depolarization speed in the septum—Vd1-Vd4 prolongation—left VDM R322. Once it reaches the left side of the septum, it uses the Purkinje system to activate the rest of myocytes of the left ventricle in this patient, and this results in Vd5-Vd8 shortening. In the right VDM R324, the pacing lead was placed in the His bundle region, and total correction of the left bundle branch block was achieved with normalization of the QRS on the standard 12-lead ECG. The normal pattern of ventricular activation resulted in a shortening of the depolarization speed in Vd1-Vd4.

Case 3: Right bundle branch block (RBBB) R45 and its correction by nonselective His bundle pacing R46. FIG. 11.

On the left, the VDM R45 of the patient with RBBB is shown. The conduction in the left Tawara branch is not affected, and so the depolarization speed under leads above left ventricle show faster myocardial depolarization (Vd5-Vd8) compared to Vd1-Vd4, where prolongation of Vd1-Vd4 means deceleration of the depolarization speed in the myocardium of the right ventricle. This prolongation is more evident in the AVd1-AVd4 parameters. The difference between Vdi and AVdi indicates a double or multiple activations in a single electrode.

On the right, the VDM R46 during pacing of the His bundle with the RBBB correction is shown. Due to restoration of the conduction through both Tawara branches depolarization speed in the right ventricle normalized, which is reflected by shortening of Vd1-Vd4 and AVd1-AVd4.

Case 4: LBBB R338 correction by biventricular pacing R339. FIG. 12

In the left, VDM R338 of the patient with LBBB is shown. The conduction block in the left Tawara branch causes depolarization deceleration in the septum (Vd3, AVd3-AVd4) and the left ventricular lateral wall (Vd6-Vd7, AVd7-AVd8).

Biventricular pacing showed in VDM 339 corrects both depolarization decelerations, but generally, the depolarization speed under most leads is nearly the same. It is because biventricular pacing relay on a slow cell to myocardial cell conduction and moreover, epi-to endocardial activation caused by LV lead is known to be approximately 5 times slower than depolarization in endo-epicardial direction.

Case 5: Pure myocardial capture of the septum R93, nonselective His bundle pacing R94. FIG. 13.

On the left VDM R93 of the pure myocardial capture of the septum of the right ventricle is shown. A sudden decrease in the speed of the depolarization could be observed under leads V4, V5, as the result of the slow electrical wave-front propagation through the interventricular septum. Also, Vd7 and Vd8 show decreased depolarization speed of the adjacent myocardium because of the slow trans-myocardial electrical wave-front propagation.

On the right VDM R94 in the same patient but during the pacing of the His bundle. His bundle pacing uses the natural conductive tissue of the heart. Because of the high velocity of the electric pulse propagation in the conductive tissue of both ventricles, concomitant, and fast depolarization of ventricular myocytes occurs and short Vd1-Vd8 parameters under all leads reflect this.

Case 6: Right bundle branch block (RBBB) R45 and its correction by nonselective His bundle pacing R46, FIG. 17, left panel. Pure myocardial capture of the septum R93, nonselective His bundle pacing R94, FIG. 17, right panel. AT, ATi, AI, and AIi parameters. The activation times ATi indicate the time position of the myocardial cells activation in the region near Vi lead. AT parameter is mean from ATi parameters. The activation index AIi is the value, which corresponds to the duration and volume of simultaneously activated myocardial cells in the region near Vi lead. AI parameter is mean from AIi parameters. Straightening the ATi vertical line implies a reduction in dyssynchrony DYS; shortening the rectangles AIi (lower AIi value) represents a local activation acceleration. Both nonselective His-bundle pacing (nsHis) cases reduce dyssynchrony and decrease AIi.

The invention claimed is:

1. A method of processing an electrocardiogram, which comprises the following steps:

measuring the electrocardiogram comprising signals in at least two channels and sensing a separate electrocardiogram signal on each of the at least two channels; wherein the measuring step is carried out by an apparatus comprising one or more analogue amplifiers each including an input and an output, the input of each of the analogue amplifiers being connected to an output of a sensor measuring the electrocardiogram signal, the apparatus further comprising one or more analogue signal to digital signal converters, each including an input and an output, the input of each of the analogue signal to digital signal converters being connected to the output of a corresponding one of the one or more analogue amplifiers, wherein the sensor, the one or more analogue amplifiers, and the one or more analogue signal to digital signal converters have the transmission bandwidth at least 0.3 kHz, and performing the following steps in a processing unit, including an input connected to the output of the analogue to digital signal converters and an output connected to at least one imaging unit:

selecting at least two frequency ranges of the signal in each of the said at least two channels;

calculating an envelope for the signal in each frequency range in each channel;

dividing the calculated envelope of the signal in each frequency range in each channel into envelopes of segments of QRS complexes;

computing, for each frequency range in each channel, an average envelope or a median envelope as an average or median of the envelopes of segments of the QRS complexes;

normalizing the average envelope or the median envelope to obtain a normalized average envelope or a normalized median envelope for each frequency range in each channel; wherein the normalization is performed by dividing the average envelope or the median envelope of each frequency range in each channel by its integral or by a maximal value reached in the average envelope or the median envelope, in each frequency range and each channel separately, while calculating the integral or the maximal value within an interval of a minimum of 50 ms before the position of the QRS complex and minimum 50 ms after the position of the QRS complex;

calculating a signal average envelope or a signal median envelope from the normalized average envelopes or the normalized median envelopes of all frequency ranges of the at least two frequency ranges within each channel; and calculating a first temporal duration (Vdi) of the signal average envelope or the signal median envelope by using a horizontal line placed crossing the signal average envelope or the signal median envelope and calculating the time length of the horizontal line, wherein the horizontal line is placed at a level corresponding to 10-70 percent of a maximal value of the signal average envelope or the signal median envelope; and/or calculating a second temporal duration (AVdi) of the signal average envelope or the signal median envelope by using the horizontal line placed intersecting the signal average envelope or the signal median envelope and calculating the time length between the first and the last intersection of the signal average envelope or the signal median envelope with the horizontal line, wherein the horizontal line is placed at a level corresponding to 10-70 percent of the maximal value of the signal average envelope or the signal median envelope;

determining a local depolarization duration of heart ventricles in units of time as the first temporal duration, and/or determining a total local depolarization duration of heart ventricles in units of time as the second temporal duration.

2. The method according to claim 1, which further comprises a step of calculating a final average envelope or a final median envelope from all of the signal average envelope or all of the signal median envelopes of the said at least two channels.

3. The method according to claim 1, wherein the step of computing an average or median envelope as an average or median of envelopes of segments of the QRS complexes for each frequency range in each channel is followed by a step of performing baseline correction for each of the average or median envelopes by subtracting mean or median value of an interval in which the QRS complex is not present, wherein the interval in which the QRS complex is not present is an interval between the QRS complexes, to remove noise background.

4. The method according to claim 1, which further comprises a step of calculating a volumetric activation index (AIi) as an area delimited by the signal average envelope or the signal median envelope and the horizontal line, wherein the horizontal line is at a level corresponding to 10-70 percent of the maximum value of the signal average envelope or the signal median envelope, wherein the value of the signal average envelope or the signal median envelope is normalized to 0 at the threshold level and 1 at the maximum level.

5. The method according to claim 4, which further comprises a step of calculating parameters Vd or AVd expressing the average depolarization activation time, wherein the Vd or AVd are calculated as a mean or median value from the Vdi or AVdi from the at least two channels; and a step of calculating parameter AI expressing the average depolarization activation volume, wherein the AI is calculated as the mean or median value from the AIi from the at least two channels.

6. The method according to claim 4, which further comprises a step of calculating a standard deviation SDVd of the AVdi or Vdi values from the at least two channels, wherein the SDVd expresses variability of the local depolarization activation duration; and a step of calculating a standard deviation SDAI of the AIi values from at least two channels, wherein the SDAI expresses variability of the local depolarization activation volume.

7. The method according to claim 4, which further comprises a step of calculating an activation time ATi as time position of a center of mass of the normalized average envelopes or the normalized median envelopes above the horizontal line crossing the normalized average envelopes or the normalized median envelopes at 10-70 percent of the maximum of the normalized average envelopes or the normalized median envelopes or time position of maximal value of the normalized average envelopes or the normalized median envelopes, and subsequently calculating activation dyssynchrony (DYS) as a time difference between the activation times of two of the ECG channels, wherein the DYS parameter indicates a time delay of ventricular depolarization between any two of the ECG channels, and wherein the highest value achieved for any combination of two of the ECG channels is used.

8. The method according to claim 7, which further comprises a step of calculating parameters Vd or AVd expressing the average depolarization activation time, wherein the Vd or AVd are calculated as a mean or median value from the Vdi or AVdi from the at least two channels; and a step of calculating parameter AI expressing the average depolarization activation volume, wherein the AI is calculated as the mean or median value from the AIi from the at least two channels; and a step of calculating relative activation dyssynchrony (RDYS) by dividing the activation dyssynchrony value DYS by the Vd, AVd, or AI values, wherein the RDYS parameter indicates the relationship between dyssynchrony and the speed or volume of depolarization propagation.

9. The method according to claim 7, which further comprises a step of calculating parameters Vd or AVd expressing the average depolarization activation time, wherein the Vd or AVd are calculated as a mean or median value from the Vdi or AVdi from the at least two channels; and a step of calculating parameter AI expressing the average depolarization activation volume, wherein the AI is calculated as the mean or median value from the AIi from the at least two channels; and a step of calculating cumulative activation dyssynchrony and depolarization duration (PDYS) by adding the value of DYS and the value of the Vd or AVd.

10. The method according to claim 7, which further comprises a step of calculating a standard deviation SDVd of the AVdi or Vdi values from the at least two channels, wherein the SDVd expresses variability of the local depolarization activation duration; and a step of calculating a standard deviation SDAI of the AIi values from at least two channels, wherein the SDAI expresses variability of the local depolarization activation volume; and a step of calculating relative activation dyssynchrony variability (SRDYS) by dividing the dyssynchrony value DYS by the SDVd or SDAI parameter, wherein the SRDYS parameter indicates the relationship between dyssynchrony and the inter-lead variability of depolarization propagation speed or volume.

11. The method according to claim 1, which further comprises a step of calculating parameters Vd or AVd expressing the average depolarization activation time, wherein the Vd or AVd are calculated as a mean or median value from the Vdi or AVdi from the at least two channels.

12. The method according to claim 1, which further comprises a step of calculating a standard deviation SDVd of the AVdi or Vdi values from the at least two channels, wherein the SDVd expresses variability of the local depolarization activation duration.

13. The method according to claim 1, wherein the electrocardiographic signals in the at least two channels are signals measured in channels of V1, V2, V3, V4, V5, V6 electrocardiography leads or V1, V2, V3, V4, V5, V6, V7 and V8 electrocardiography leads.

14. The method according to claim 1, which further comprises a step of constructing a ventricular depolarization matrix by representing each row of the ventricular depolarization matrix by the normalized average envelope or the normalized median envelope for one of the said at least two ECG channels;
detecting minimal and maximal value in each row of the ventricular depolarization matrix, assigning the minimal value to a first color, and assigning the maximal value to a second color;
assigning colors to the values between the minimum and the maximum within the color range from the first color to the second color with linear or nonlinear color transition.

15. The method according to claim 1, which further comprises a step of calculating an activation time ATi as time position of a center of mass of the normalized average envelopes or the normalized median envelopes above the horizontal line crossing the normalized average envelopes or the normalized median envelopes at 10-70 percent of the maximum of the normalized average envelopes or the normalized median envelopes or time position of maximal value of the normalized average envelopes or the normalized median envelopes, and subsequently calculating activation dyssynchrony (DYS) as time difference between the activation times of two of the ECG channels, wherein the DYS parameter indicates a time delay of ventricular depolarization between any two of the ECG channels, and wherein the highest value achieved for any combination of two of the ECG channels is used.

16. The method according to claim 15, which further comprises a step of calculating parameters Vd or AVd expressing the average depolarization activation time, wherein the Vd or AVd are calculated as a mean or median value from the Vdi or AVdi from the at least two channels; and a step of calculating relative activation dyssynchrony (RDYS) by dividing the activation dyssynchrony value DYS by the Vd or AVd, wherein the RDYS parameter indicates the relationship between dyssynchrony and the speed of depolarization propagation.

17. The method according to claim 15, which further comprises a step of calculating cumulative activation dyssynchrony and depolarization duration (PDYS) by adding the value of DYS and the value of Vd or AVd.

18. The method according to claim 15, which further comprises a step of calculating a standard deviation SDVd of the AVdi or Vdi values from the at least two channels, wherein the SDVd expresses variability of the local depolarization activation duration; and a step of calculating relative activation dyssynchrony variability (SRDYS) by dividing the dyssynchrony value DYS by the SDVd parameter, wherein the SRDYS parameter indicates the relationship between dyssynchrony and the inter-lead variability of depolarization propagation speed.

* * * * *

UNITED STATES PATENT AND TRADEMARK OFFICE
CERTIFICATE OF CORRECTION

| | |
|---|---|
| PATENT NO. | : 11,517,243 B2 |
| APPLICATION NO. | : 17/104928 |
| DATED | : December 6, 2022 |
| INVENTOR(S) | : Pavel Jurak et al. |

It is certified that error appears in the above-identified patent and that said Letters Patent is hereby corrected as shown below:

On the Title Page

Item (73) should read:
(73) Assignees: INSTITUTE OF SCIENTIFIC INSTRUMENTS OF THE CZECH ACADEMY OF SCIENCES, V.V.I., Brno (CZ); ST. ANNE'S UNIVERSITY HOSPITAL BRNO, Brno (CZ); CHARLES UNIVERSITY, Prague (CZ); CARDION S.R.O., Brno (CZ)

Signed and Sealed this
Seventh Day of March, 2023

Katherine Kelly Vidal
*Director of the United States Patent and Trademark Office*